(12) United States Patent
Chen et al.

(10) Patent No.: US 9,827,053 B2
(45) Date of Patent: Nov. 28, 2017

(54) INTRAOPERATIVE TRACKING METHOD

(71) Applicants: Chieh-Hsiao Chen, Taichung (TW); Kuan-Ju Wang, Hsinchu County (TW)

(72) Inventors: Chieh-Hsiao Chen, Taichung (TW); Kuan-Ju Wang, Hsinchu County (TW)

(*) Notice: Subject to any disclaimer, the term of this patent is extended or adjusted under 35 U.S.C. 154(b) by 69 days.

(21) Appl. No.: 15/173,512

(22) Filed: Jun. 3, 2016

(65) Prior Publication Data
US 2016/0354157 A1   Dec. 8, 2016

Related U.S. Application Data

(60) Provisional application No. 62/171,245, filed on Jun. 5, 2015.

(51) Int. Cl.
*G06K 9/00* (2006.01)
*A61B 34/10* (2016.01)
(Continued)

(52) U.S. Cl.
CPC .............. *A61B 34/10* (2016.02); *A61B 34/30* (2016.02); *A61B 2034/105* (2016.02);
(Continued)

(58) Field of Classification Search
None
See application file for complete search history.

(56) References Cited

U.S. PATENT DOCUMENTS 6,122,541 A    9/2000 Cosman
9,271,682 B2 *  3/2016 Cerofolini .............. A61B 5/055
(Continued)

FOREIGN PATENT DOCUMENTS

CN    1243690    2/2000
CN   102999902   3/2013
(Continued)

OTHER PUBLICATIONS

International Search Report and Written Opinion from PCT/CN2016/084732.

*Primary Examiner* — Nancy Bitar
(74) *Attorney, Agent, or Firm* — Haverstock & Owens LLP

(57) ABSTRACT

One example method to determine an actual surgical pathway of a patient based on a planned surgical pathway may include retrieve a first two-dimensional image of the patient associated with information collected at a first point in time. A first coordinate system describes a spatial relationship between the patient and an apparatus in an operating room. The method further includes modifying a three-dimensional model of the patient including the planned surgical pathway with a first set of modification parameter values. A second coordinate system describes the three-dimensional model constructed by information collected at a second point in time earlier than the first point in time. The method further includes retrieving a second two-dimensional image from the modified three-dimensional model, computing a first correlation between the first two-dimensional image and the second two-dimensional image; and transforming the planned surgical pathway to the first coordinate system based on the first set of modification parameter values to identify the actual surgical pathway.

20 Claims, 7 Drawing Sheets

(51) Int. Cl.
   *A61B 34/30*      (2016.01)
   *A61B 90/00*      (2016.01)

(52) U.S. Cl.
   CPC ... *A61B 2034/107* (2016.02); *A61B 2090/364* (2016.02); *A61B 2090/376* (2016.02); *A61B 2090/378* (2016.02)

(56) References Cited

U.S. PATENT DOCUMENTS

| | | | | |
|---|---|---|---|---|
| 2004/0215071 | A1* | 10/2004 | Frank | A61B 6/4441 |
| | | | | 600/407 |
| 2007/0167801 | A1* | 7/2007 | Webler | G06F 19/3437 |
| | | | | 600/459 |
| 2012/0010501 | A1* | 1/2012 | Cerofolini | A61B 5/055 |
| | | | | 600/427 |
| 2013/0218024 | A1* | 8/2013 | Boctor | A61B 8/0841 |
| | | | | 600/476 |
| 2014/0018668 | A1* | 1/2014 | Zheng | A61B 8/4254 |
| | | | | 600/424 |
| 2015/0077528 | A1 | 3/2015 | Awdeh | |
| 2016/0035093 | A1* | 2/2016 | Kateb | A61B 6/5247 |
| | | | | 382/131 |

FOREIGN PATENT DOCUMENTS

| | | |
|---|---|---|
| CN | 103142313 | 6/2013 |
| EP | 1715788 | 9/2011 |

\* cited by examiner

305

306

US 9,827,053 B2

INTRAOPERATIVE TRACKING METHOD

CROSS REFERENCE TO RELATED APPLICATION

The present disclosure claims the benefit of priority of the U.S. Provisional Application No. 62/171,245, filed Jun. 5, 2015, entitled "A METHOD OF BRAIN NAVIGATION GUIDANCE." The provisional application, including any appendices or attachments therefore, is hereby incorporated by reference in its entirety.

FIELD OF THE DISCLOSURE

The present disclosure relates to intraoperative tracking approaches, and more particularly to approaches to determine a surgical pathway.

BACKGROUND

Common brain diseases, such as brain tumors, Parkinson's disease, and epilepsy, not only adversely affect the patients' quality of life but sometimes can also directly contribute to the patients' death. Invasive surgical procedures are usually performed after conservative treatments, such as medication or physical therapy that fails to relieve the patients' symptoms.

Generally, a surgeon may plan a surgical pathway to reach a targeted surgical site based on certain pre-operative data. However, the planned pathway may need to be altered due to changed conditions that occur after the collection of the pre-operative data. Some example of the changed conditions include a change of the patient's position on the operating table, a change in the patient's physiological condition, or the insertion of the surgical instrument itself. Any deviation from the pre-operative planned pathway often leads to further complications or an increased mortality rate.

SUMMARY

In accordance with one embodiment of the present disclosure, a method to determine an actual surgical pathway of a patient based on a planned surgical pathway is disclosed. The method includes retrieving a first two-dimensional image of the patient associated with information collected at a first point in time, modifying a three-dimensional model of the patient including the planned surgical pathway with a first set of modification parameter values, retrieving a second two-dimensional image from the modified three-dimensional model, and computing a first correlation between the first two-dimensional image and the second two-dimensional image. A first coordinate system may describe a spatial relationship between the patient and an apparatus in an operating room. A second coordinate system may describe the three-dimensional model, which may be constructed by information collected at a second point in time earlier than the first point in time. In response to the first correlation exceeding a threshold, the method further includes transforming the planned surgical pathway in the second coordinate system to the first coordinate system based on the first set of modification parameter values to identify the actual surgical pathway.

In accordance with another embodiment of the present disclosure, a non-transitory computer-readable storage medium is disclosed. The non-transitory computer-readable storage medium may contain a set of executable instructions. In response to execution by a processor in one of one or more surgical system, the processor is configured to retrieve a first two-dimensional image of the patient associated with information collected at a first point in time, modify a three-dimensional model of the patient including the planned surgical pathway with a first set of modification parameter values, retrieve a second two-dimensional image from the modified three-dimensional model, and compute a first correlation between the first two-dimensional image and the second two-dimensional image. A first coordinate system may describe a spatial relationship between the patient and an apparatus in an operating room. A second coordinate system may describe the three-dimensional model, which may be constructed by information collected at a second point in time earlier than the first point in time. In response to the first correlation exceeding a threshold, the processor is configured to transform the planned surgical pathway in the second coordinate system to the first coordinate system based on the first set of modification parameter values to identify the actual surgical pathway.

In accordance with other embodiments of the present disclosure, a surgical system configured to determine an actual surgical pathway of a patient based on a planned surgical pathway is disclosed. The surgical system may include a storage system, a robotic arm, an image collection apparatus, and a processor. The processor may be configured to retrieve a first two-dimensional image of the patient associated with information collected by the image collection apparatus at a first point in time from the storage system, modify a three-dimensional model of the patient including the planned surgical pathway with a first set of modification parameter values, retrieve a second two-dimensional image from the modified three-dimensional model from the storage system, and compute a first correlation between the first two-dimensional image and the second two-dimensional image. A first coordinate system may describe a spatial relationship between the patient and the robotic arm. A second coordinate system may describe the three-dimensional model, which is constructed by information collected at a second point in time earlier than the first point in time. In response to the first correlation exceeding a threshold, the processor is configured to transform the planned surgical pathway in the second coordinate system to the first coordinate system based on the first set of modification parameter values to identify the actual surgical pathway, and instruct the robotic arm to perform the surgery based on the actual surgical pathway.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1A:
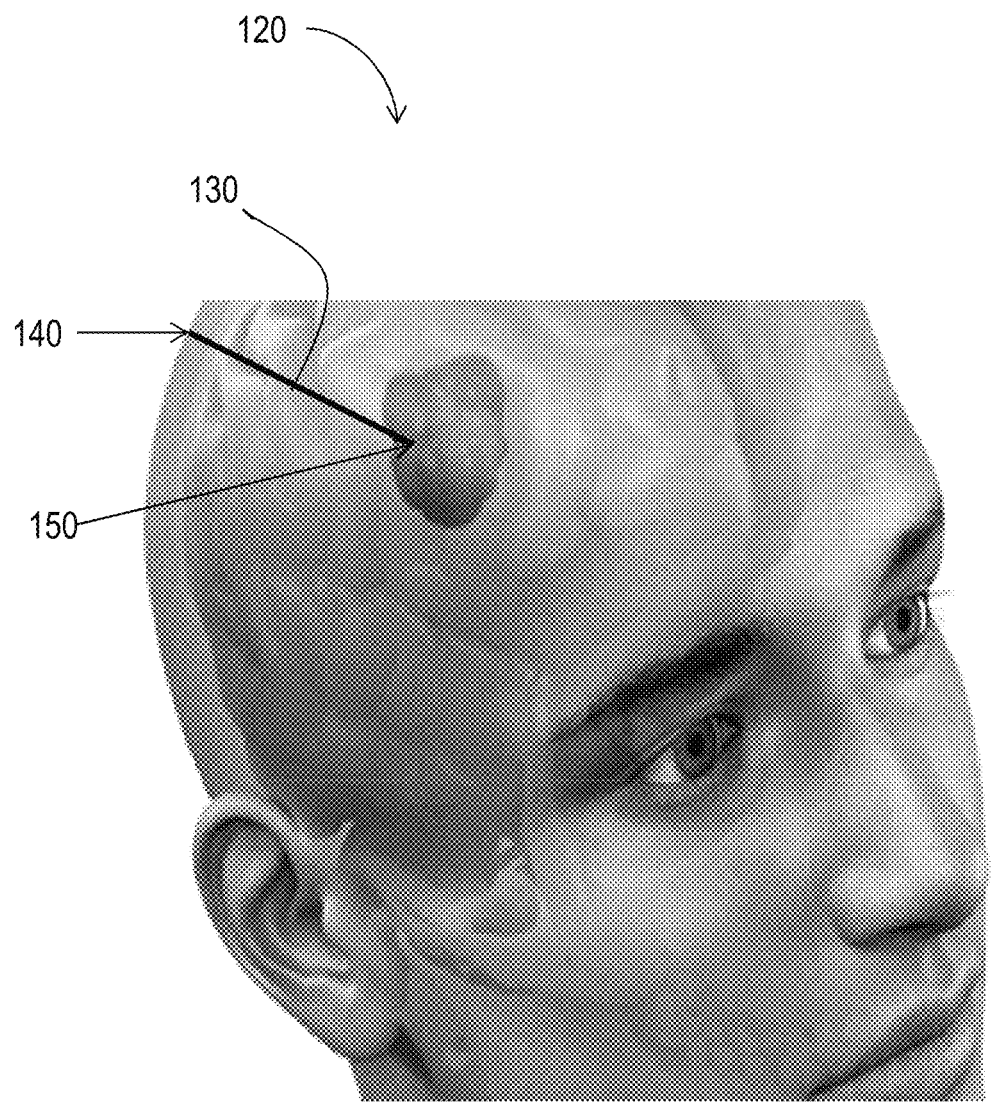
FIG. 1A is an example figure showing the spatial relationships among several points that may be encountered during an operation.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated herein.

This disclosure is drawn, inter alia, to methods, apparatuses, and systems related to an intraoperative surgical pathway determination based on two sets of images collected at two different spaces and two different points in time. In the disclosure, the term "projection" generally refers to an approach of mapping three-dimensional points to a two-dimensional plane. The term "surgical pathway" may refer to a pathway comprising a surgical entry point, a targeted surgical site, and a path between the surgical entry point and the targeted surgical site. Throughout the disclosure, the terms "surgical procedure" and "surgery" are used interchangeably.

FIG. 1A is an example figure showing the spatial relationships among several points that may be encountered during an operation, arranged in accordance with some embodiments of the present disclosure. In a three-dimensional image 120, a surgical pathway 130 includes a surgical entry point 140 and a targeted surgical site 150.

Figure 1B:
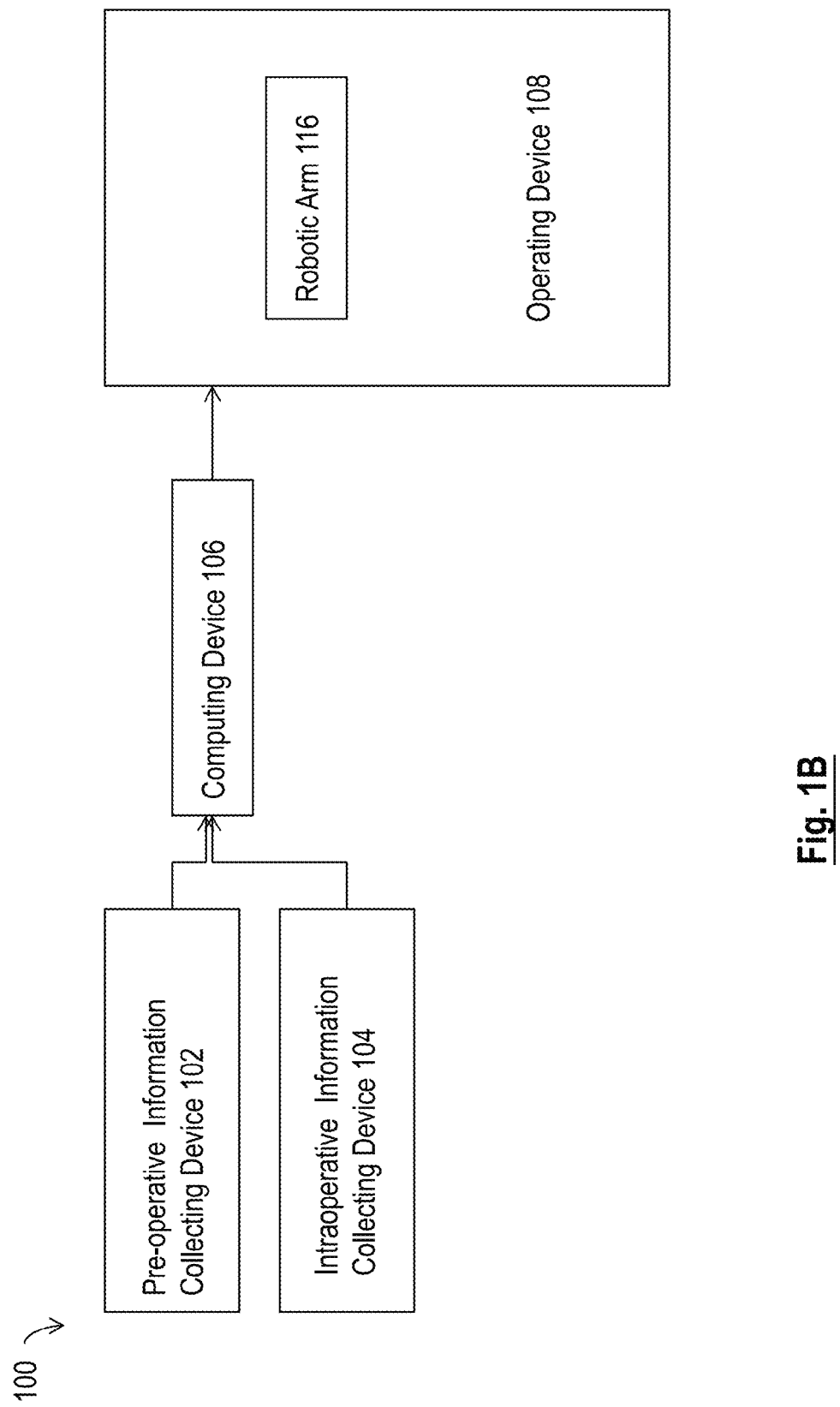
FIG. 1B is an example block diagram showing the configuration of a surgical guiding and positioning system.

FIG. 1B is an example block diagram showing the configuration of a surgical guiding and positioning system 100, arranged in accordance with some embodiments of the present disclosure. The surgical guiding and positioning system 100 mainly includes a pre-operative information collection device 102, an intraoperative information collection device 104, a computing device 106, and a surgical instrument 108 including a robotic arm 116. The blocks are only provided as examples, and some of the blocks may be optional, combined into fewer blocks, or expanded into additional blocks without detracting from the essence of the disclosed embodiments.

The pre-operative information collection device 102 is configured to collect overall information of a surgical site, such as a specific site of a brain, before a surgical procedure begins. In some embodiments, the overall information can be acquired through computed tomography (CT), magnetic resonance imaging (MRI), surface scan, X-ray scan, ultrasound scan, and etc. Given the size of these devices and hospital management perspectives, a pre-operative information collection device is usually placed in a space that differs from the operating room, where the surgical procedure is actually performed. With the overall information (e.g. the intracranial anatomy, the target or lesion location, the surface land markings, or the surface anatomy) of the surgical site, a surgeon may plan a surgical pathway some time before a surgical procedure begins.

The intraoperative information collection device 104 is configured to collect the surface anatomy information of the patient around the surgical site immediately before a surgical incision is made in the operating room. Some examples of the intraoperative information collection device 104 may include, without limitation, a camera, an infrared camera, an X-ray module, an ultrasonic scanner, and others. The intraoperative information collection device 104 may collect the patient's surface anatomy information when the patient is on the operating table in the operating room.

The computing device 106 may be configured to (1) process information collected by the pre-operative information collection device 102, (2) process information collected by the intraoperative information collection device 104, and/or (3) determine a surgical pathway based on the processed information. Additional details will be provided in subsequent paragraphs.

The surgical instrument 108 may include a robotic arm 116, which is configured to perform the surgery. The surgical instrument 108 is configured to receive information associated with the determined surgical pathway from the computing device 106. The received information may include some coordinate data and vectors that are recognizable by the robotic arm 116. In other words, the robotic arm 116 may perform the surgery according to the coordinate data and vectors.

Figure 2:
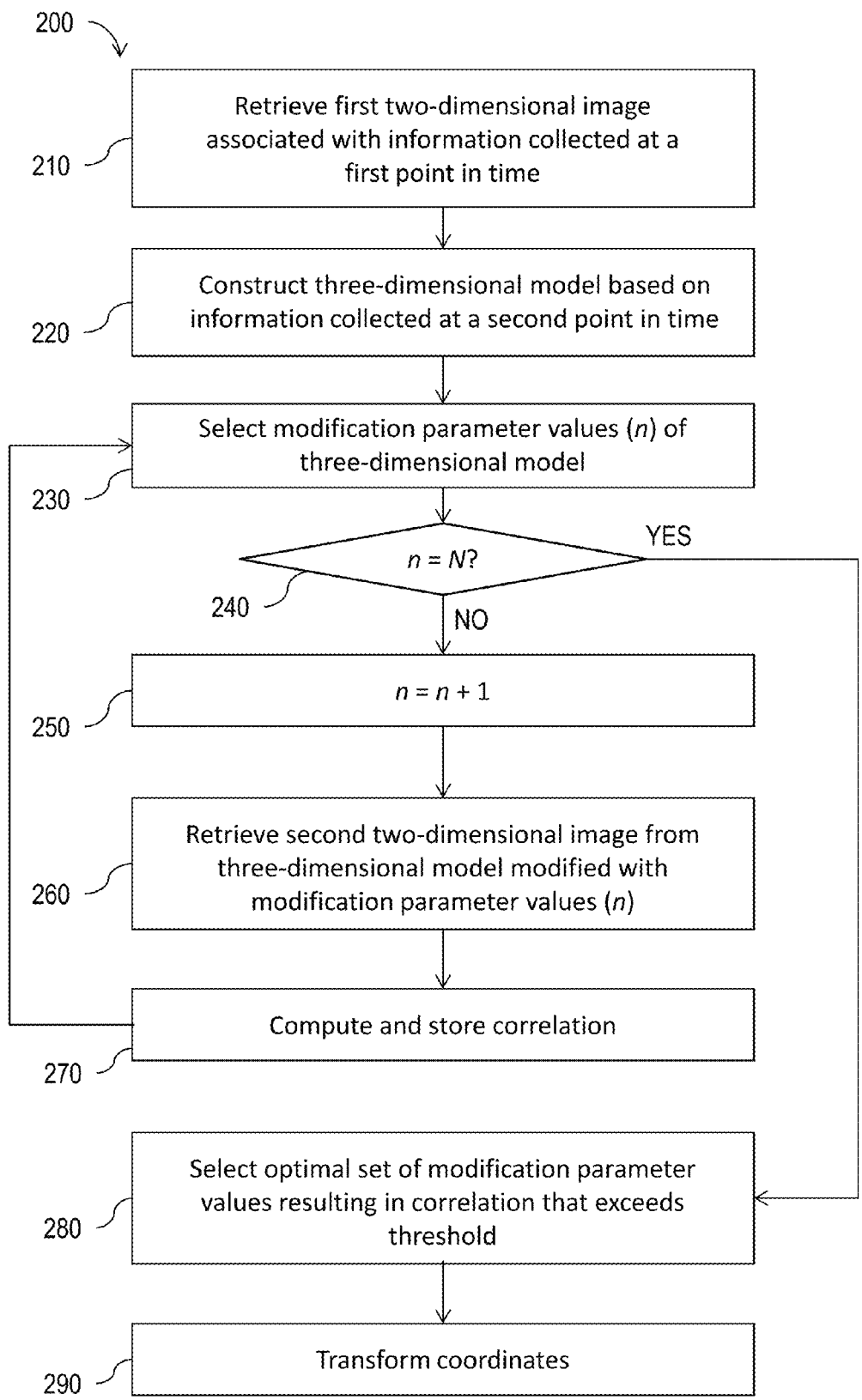
FIG. 2 is flow diagram illustrating an example process to determine a surgical pathway.

FIG. 2 is a flow diagram illustrating an example process 200 to determine a surgical pathway, in accordance with some embodiments of the present disclosure. Process 200 may include one or more operations, functions, or actions as illustrated by blocks 210, 220, 230, 240, 250, 260, 270, 280, and/or 290 which may be performed by hardware, software and/or firmware. The various blocks are not intended to be limiting to the described embodiments. The outlined steps and operations are only provided as examples, and some of the steps and operations may be optional, combined into fewer steps and operations, or expanded into additional steps and operations without detracting from the essence of the disclosed embodiments. Although the blocks are illustrated in a sequential order, these blocks may also be performed in parallel, and/or in a different order than those described herein.

Process 200 may begin at block 210, "retrieve first two-dimensional image associated with information collected at a first point in time." In some embodiments, the collected information may correspond to surface anatomy information of the patient, and the first point in time may correspond to a time immediately prior to a surgical incision is made. Some example first point in time may include, without limitation, the start of the day of the surgery, the time the patient on the operating table in the operating room, and any points of time therebetween. In addition, the first two-dimensional image may be a photo taken by a camera (e.g., an infrared camera). For example, in a brain surgery, the camera may be configured to take a picture of the patient's head immediately prior to a surgical incision is made on the patient's head in the operating room. The camera may be fixed at a stationary device (e.g., a robotic arm) in the operating room so that the camera and the patient main maintain a constant relationship in the operating room. In some embodiments, the camera may take photos from different positions while the robotic arm is moving. Each position may correspond to a specific photo. In some embodiments, a first coordinate system may be used to define the spatial relationship between the surface anatomical parts of the patient (e.g., nose, eyes, other facial features), and the robotic arm in the operating room.

Block 210 may be followed by block 220, "construct three-dimensional model based on information collected at a second point in time." Before a surgical procedure is performed, some medical imaging techniques may be used to capture a snapshot of the patient's conditions, so that a surgical plan may be formulated. Suppose the surgical site is the brain of the patient. The surgeon may order a medical image scan (e.g., CT or MRI) of the brain. Such medical image scan may perform 3 to 5 days prior to the surgery. A three-dimensional model may be constructed based on the medical scan data using some known approaches. A second coordinate system may be used to define the spatial relationship between the planned surgical pathway and certain anatomical parts of the patient.

Block 220 may be followed by block 230, "select modification parameter values (n) of three-dimensional model." The three-dimensional model constructed in block 220 may be modified with some modification parameter values. Example modification parameters may include, without limitation, a scaled ratio, a rotation degree, and a translation vector. These modification parameters may be used to modify the three-dimensional model to better reflect a patient's condition immediately prior to the surgery. To find the optimal set of modification parameter values, in some embodiments, N sets of modification parameter values may be obtained. Here, n may be between an integer between 1 and N. However, it should be apparent to one with ordinary skills in the art to employ any other technically feasible approaches to perform the iterations without exceeding the scope of the present disclosure.

In one example, the constructed three-dimensional model may be represented in a Cartesian coordinate system. The scaled ratio refers to a constant proportional ratio of a linear dimension in every axis of the Cartesian coordinate system. Similarly, the rotation degrees may refer to a rotation around a specific axis in the Cartesian coordinate system. The translation vector may refer to a movement vector in the Cartesian coordinate system.

Block 230 may be followed by block 240, "n=N?" If n does not equal to N, then block 240 may be followed by block 250, where n is incremented by 1. On the other hand, if n equals to N, then block 240 may be followed by block 280, "select optimal set of modification parameter values resulting in correlation that exceeds threshold," because all of the correlation computation using the N sets of modification parameter values have been completed. If none of the correlation computation results using the N sets of modification parameter values exceed threshold, process 200 may reset n and go back to block 230 to select a new set of modification parameter values (n) of three-dimensional model that have not been selected in previous iterations.

In block 260, a second two-dimensional image may be the projection of the three-dimensional model modified with the selected set of modification parameter values (n). In other words, the second two-dimensional image may correspond to a specific set of modification parameter values. The projection may be done by any technically feasible approach, such as parallel projection, orthographic projection, perspective projection, etc. The second two-dimensional image retrieved in block 260 may be compared to the first two-dimensional image retrieved in block 210, and the process goes to block 270, "compute and store correlation."

In block 270, in some embodiments, a correlation between a first region of interest of the first two-dimensional image and a second region of interest of the second two-dimensional image is computed and stored. The first region of interest and the second region of interest may be selected according to the contour features of the first two-dimensional image and the second two-dimensional image, respectively. The selection may be based on historic data or surgeon's experience. The correlation may be calculated by some known approaches. For example, the correlation may be calculated with Equation 1 below:

$$\text{corr} = \frac{\sum_{i=0}^{N} P_1[k_1[i]] P_2[k_2[i]]}{\sqrt{\sum_{i=0}^{N} P_1[k_1[i]]^2 \sum_{i=0}^{N} P_2[k_2[i]]^2}} \quad (1)$$

where:
N is the number of points in the first region of interest;
$P_1$ is an indexed array including data of the second two-dimensional image;
$P_2$ is an indexed array including data of the first two-dimensional image;
$k_1$ is an indexed array including serial i values of successive pixels in a region of $P_1$ where the correlation is to be computed; and
$k_2$ is an indexed array including serial i values of successive pixels in a region of $P_2$ where the correlation is to be computed.

With different sets of modification parameter values, different corresponding correlations are calculated and stored in block 270.

In some embodiments, edge detection is performed on the first two-dimensional image and the second two-dimensional image. The correlation may be calculated between the edge detected version of the first two-dimensional image and the edge detected version of the second two-dimensional image. Some example edge detection may include, without limitation, Canny edge detection approach, first-order edge detection approaches, and second-order edge detection approaches.

After processing blocks 230, 240, 250, 260, and 270 in N iterations, the three-dimensional model is modified by N sets of modification parameter values. With the N number of modified dimensional models, N number of the second two-dimensional images are then retrieved and used to perform the aforementioned correlation. Process 200 may be followed by block 280, "select optimal set of modification parameter values resulting in correlation that exceeds threshold." To determine whether the first two-dimensional image and the second two-dimensional image are sufficiently correlated, a threshold value is set. The threshold value may be determined based on some historical data (e.g., data collected from animal testing or other patients). Alternatively, the threshold value may be determined based on the surgeon's experience. Any of the stored correlations that exceed the threshold value would indicate that the first region of interest and the second region indeed correspond to the same anatomical part of the patient. Out of these stored correlations that exceed the threshold value, in one embodiment, the set of modification parameter values resulting in the maximum correlation is selected as the optimal set of modification parameter values.

Block 280 may be followed by block 290, "transform coordinate," where the coordinates of the second coordinate system are transformed to the first coordinate system based on the selected optimal set of modification parameter values. Therefore, the planned surgical pathway in the second coordinate system may be transformed to the first coordinate system, which is used to represent the operating room in which the surgical procedure is actually performed. Based on the transformed coordinates and vectors in the first coordinate system, a robotic arm may be configured to perform the surgical procedure, having taken into account of changing conditions associated with the patient.

Figure 3A:
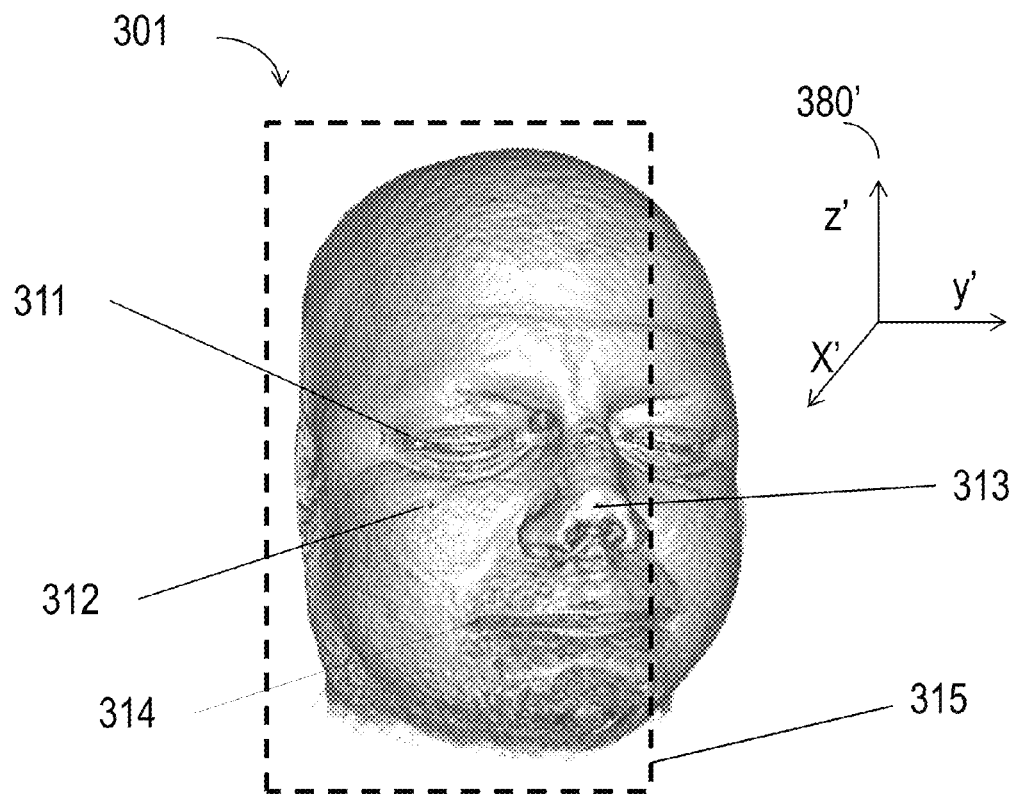
FIG. 3A shows an example two-dimensional image associated with information collected at a first point in time.

FIG. 3A shows an example two-dimensional image 301 associated with information collected at a first point in time (e.g., right before a surgical incision is made on a patient in the operating room, usually collected within 24 hours prior to the surgical incision), arranged in accordance with some embodiments of the present disclosure. The two-dimensional image 301 may be taken by an infrared camera. The two-dimensional image may include some surface anatomical parts of the patient, for example, right eye 311, cheek curve 312, nose 313, and mouth 314. A first region of interest 315 of the two-dimensional image 301 may be selected to compare with a second region of interest of another two-dimensional image and will be described in details below. The first region of interest 315 may cover some surface anatomical parts, for example, right eye 311, cheek curve 312, nose 313, and mouth 314. A first coordinate system 380' may be used to describe the spatial relationship between devices (e.g., robotic arm) in the operating room and surface anatomical parts of the patient.

Figure 3B:
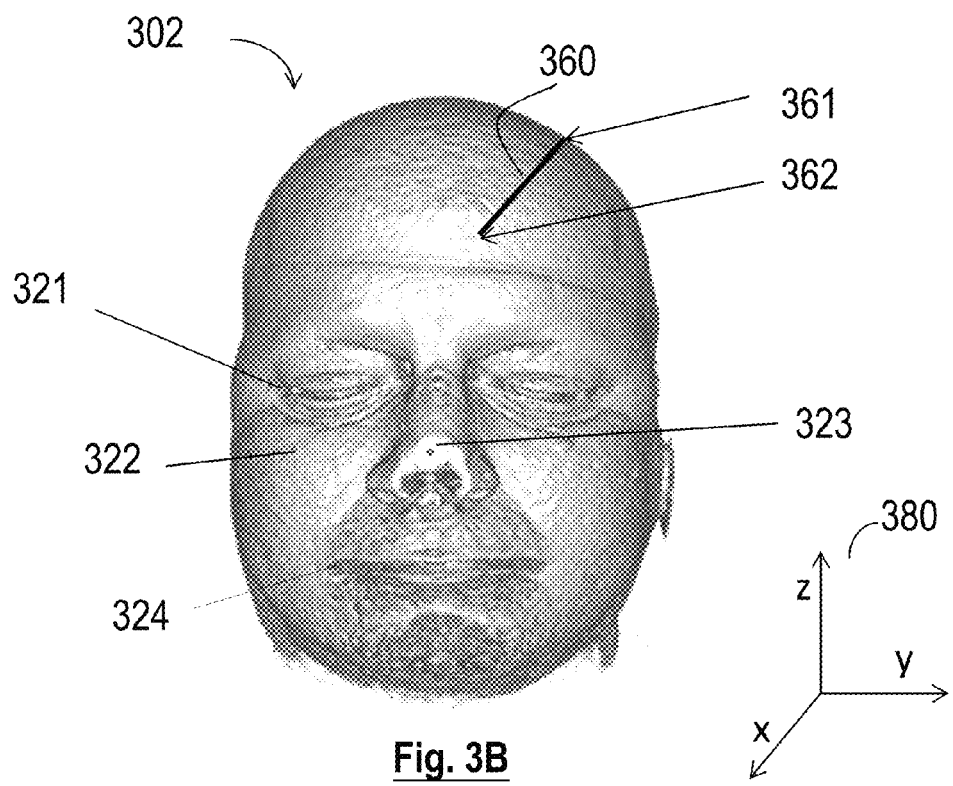
FIG. 3B shows an example three-dimensional model constructed based on data collected at a second point in time.

FIG. 3B shows an example three-dimensional model 302 constructed based on data collected at a second point of time (e.g., before the date of a surgical procedure, usually collected within 3 days prior to the surgical procedure), arranged in accordance with some embodiments of the present disclosure. The three-dimensional model 302 includes surface anatomical parts, for example, right eye 321, cheek curve 322, nose 323, and mouth 324. A surgical pathway 360 may be planned on the three-dimensional model 302 according to the medical scan image 302'. The surgical pathway 360 may start with a surgical entry point 361 and end at a target surgical site 362. As discussed earlier in conjunction with FIG. 1A, the surgical entry point 361 may be on the skull of the patient and the target surgical site 362 may be a tumor in patient's brain.

In some embodiments, a Cartesian second coordinate system 380 may be used to describe the spatial relationship among the surgical pathway 360 and right eye 321, cheek curve 322, nose 323, and mouth 324. For example, in the second coordinate system 380, the surgical entry point 361 may have a coordinate of (1, 2, 3), the target surgical site 362 may have a coordinate of (2, 3, 4) and a vector between the surgical entry point 361 and the target surgical site 362 is (1, 1, 1). Similarly, right eye 321 may have a coordinate of (4, 5, 6), cheek curve 322 may have a coordinate of (2, 9, 11), nose 323 may have a coordinate of (7, 8, 9), and mouth 324 may have a coordinate of (3, 7, 5) in the second coordinate system 380.

The three-dimensional model 302 may be modified with a set of modification parameter values to generate a modified three-dimensional model 302'. For example, a first example set of modification parameter values may include, without limitation, a scaled ratio of 100%, $\alpha$ is 45 degrees, $\beta$ is 0 degree, and $\gamma$ is 0 degree, in which $\alpha$ represents a rotation around z-axis in the second coordinate system 380, $\beta$ represents a rotation around y-axis in the second coordinate system 380, and $\gamma$ represents a rotation around x-axis in the second coordinate system 380. A second two-dimensional image may be retrieved from the modified three-dimensional model 302'. In some embodiments, the second two-dimensional image is a projection of the three-dimensional model 302'.

Figure 3C:
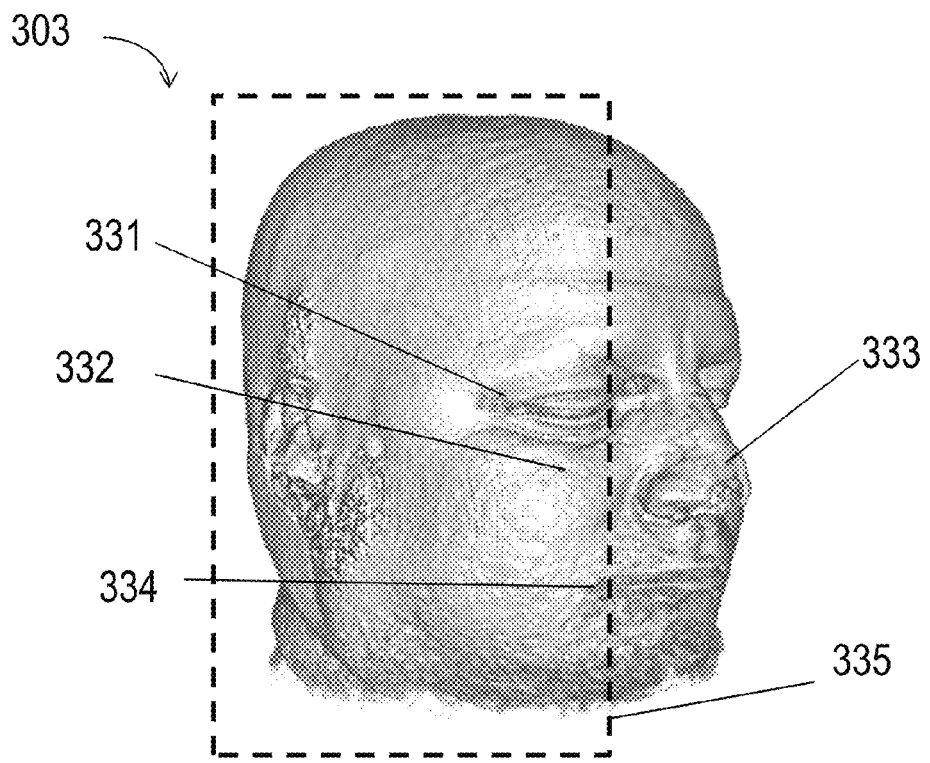
FIG. 3C shows an example projection of a modified three-dimensional model modified with a first set of modification parameter values.

FIG. 3C shows an example projection 303 of a modified three-dimensional model 302', which is modified with the first example set of modification parameter values, arranged in accordance with some embodiments of the present disclosure. FIG. 3C may include surface anatomical parts of the patient, for example, right eye 331, cheek curve 332, nose 333, and mouth 334. In conjunction with 3A, a second region of interest 335 may be selected to calculate a first correlation between the first region of interest 315 and the second region of interest 335.

Figure 3D:
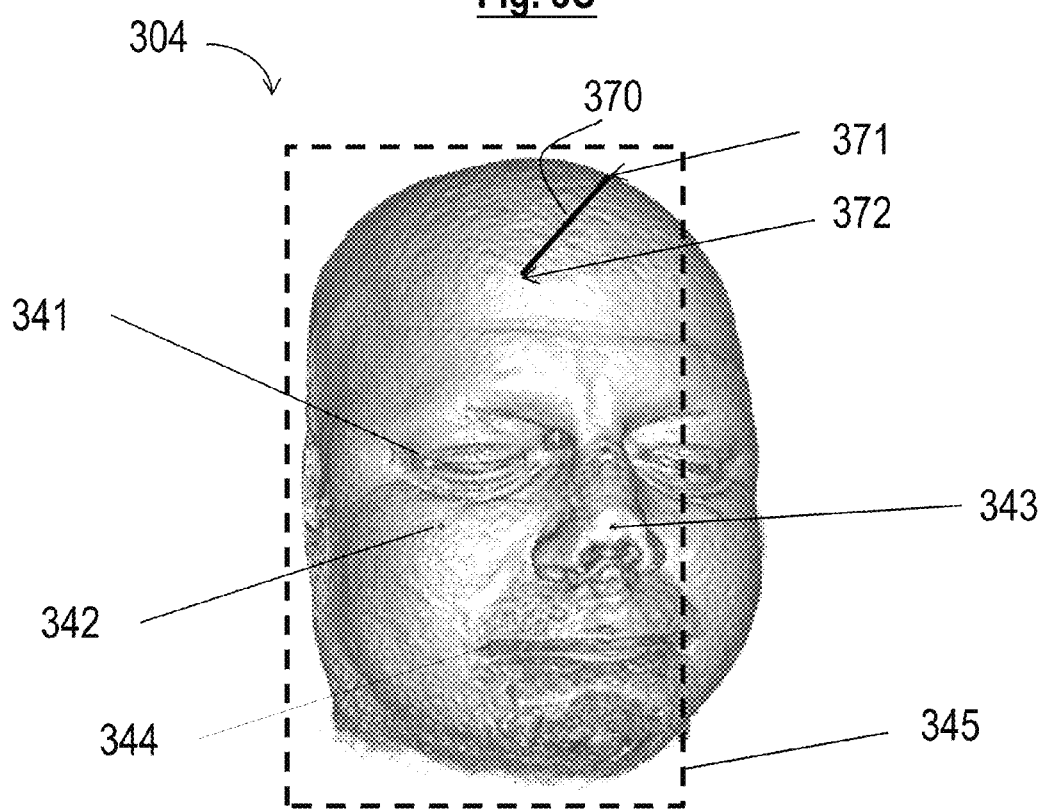
FIG. 3D shows an example projection of a modified three-dimensional model modified with a second set of modification parameter values.

After obtaining the first correlation, a second example set of modification parameter values may be used to modify the three-dimensional model to generate another modified three-dimensional model 302'. The second set example set of modification parameter values may include, without limitation, a scaled ratio of 100%, $\alpha$ is 20 degrees, $\beta$ is 0 degree, and $\gamma$ is 0 degree. Similarly, an example projection of the modified three-dimensional model 302' may be retrieved. FIG. 3D shows the example projection 304 of the modified three-dimensional model 302' modified with the second example set of modification parameter values, arranged in accordance with some embodiments of the present disclosure. FIG. 3D may include surface anatomical parts of the patient, for example, right eye 341, cheek curve 342, nose 343, and mouth 344. In conjunction with 3A, a second region of interest 345 may be selected to calculate a second correlation between the first region of interest 315 and the second region of interest 345.

Figure 3E:
FIG. 3E shows one example edge detection processed image.
Figure 3F:
FIG. 3F shows another example edge detection processed image.

In some embodiments, the two-dimensional images 301, 303, and 304 are processed first before calculating the first and second correlations. For example, an edge detection approach may be applied to process the two-dimensional images 301, 303, and 304. FIG. 3E shows one example edge detection processed image 305 of the image 301, arranged in accordance with some embodiments of the present disclosure. FIG. 3F shows another example edge detection processed image 306 associated with a modification parameter value $\alpha$ of $-45$ degrees, arranged in accordance with some embodiments of the present disclosure.

Assuming only two sets of modification parameter values (i.e., a scaled ratio of 100%, $\alpha$ is 45 degrees, $\beta$ is 0 degree, and $\gamma$ is 0 degree; and a scaled ratio of 100%, $\alpha$ is 20 degrees, $\beta$ is 0 degree, and $\gamma$ is 0 degree) are obtained to modify the three-dimensional model 302, the first correlation and the second correlation are compared with a threshold to determine which one may be the optimal set of modification parameter values. The optimal set of modification parameter values are used to transform the coordinates in the second coordinate system 380 to the first coordinate system 380'.

In some embodiments, assuming the modification parameter is associated with a scaling ratio, the transformation from the second coordinate system 380 to the first coordinate system 380' may comprise multiplying the scaled ratio to the coordinates of the second coordinate system 380. Therefore, the vector of the planned surgical pathway keeps the same in the first coordinate system 380 as in the second coordinate system 380'. However, compared to the distance of the planned surgical pathway in the second coordinate system 380, the distance of the actual surgical pathway in the first coordinate system 380' is scaled with the scaled ratio.

In some other embodiments, assuming the modification parameter is associated with a rotation angle. Therefore, the vector of the planned surgical pathway is changed in the first coordinate system 380 which will not be the same as the vector in the second coordinate system 380'. The transformation from the second coordinate system 380 to the first coordinate system 380' may comprise a matrix operation. The matrix may be a transformation matrix between the first coordinate system 380' and the second coordinate system 380. One example transformation matrix may be:

$$T_{MR}^{IR} = \begin{bmatrix} \cos\alpha\cos\beta & \cos\alpha\sin\beta\sin\gamma - \sin\alpha\cos\gamma & \cos\alpha\sin\beta\cos\gamma & x_{\text{offset}} \\ \sin\alpha\cos\beta & \sin\alpha\sin\beta\sin\gamma + \cos\alpha\cos\gamma & \sin\alpha\sin\beta\cos\gamma - \cos\alpha\sin\gamma & y_{\text{offset}} \\ -\sin\beta & \cos\beta\sin\gamma & \cos\beta\cos\gamma & z_{\text{offset}} \\ 0 & 0 & 0 & 1 \end{bmatrix}$$

where
$\alpha$ represents a rotation around z-axis in the second coordinate system 380;
$\beta$ represents a rotation around y-axis in the second coordinate system 380;
$\gamma$ represents a rotation around x-axis in the second coordinate system 380;
$x_{\text{offset}}$ represents a displacement along the x-axis in the second coordinate system 380;
$y_{\text{offset}}$ represents a displacement along the y-axis in the second coordinate system 380; and
$z_{\text{offset}}$ represents a displacement along the z-axis in the second coordinate system 380;
The coordinate transformation may be achieved with the following operation:

$$\begin{bmatrix} x' \\ y' \\ z' \end{bmatrix} = T_{MR}^{IR} \begin{bmatrix} x \\ y \\ z \end{bmatrix} \quad (3)$$

where x', y', and z' are the transformed coordinates in the first coordinate system 380' and x, y, and z are the coordinates in the second coordinate system 380.

Assuming the second set of modification parameter values (i.e., scaled ratio of 100%, $\alpha$ is 20 degrees, $\beta$ is 0 degree, and $\gamma$ is 0 degree) exceeds the threshold while the first set of modification parameter values (i.e., scaled ratio of 100%, $\alpha$ is 45 degrees, $\beta$ is 0 degree, and $\gamma$ is 0 degree) does not exceed the threshold, the second set of modification parameter values may be selected as the optimal set of modification parameter values and the transformation matrix may be:

$$T_{MR}^{IR} = \begin{bmatrix} 0.939693 & -0.34202 & 0 & 0 \\ 0.34202 & 0.939693 & 0 & 0 \\ 0 & 0 & 1 & 0 \\ 0 & 0 & 0 & 1 \end{bmatrix}$$

According to equation (3) and the transformation matrix above, in the first coordinate system 380', the surgical entry point 371 may have a coordinate of (1.62373, 1.53737, 3), the target surgical site 372 may have a coordinate of (2.90545, 2.13504, 4) and a vector between the surgical entry point 371 and the target surgical site 372 is (1.28172, 0.59767, 1). The coordinates and vector may be transmitted to the robotic arm in the operating room so that a surgeon may use the robotic arm to perform the surgery.

Figure 4:
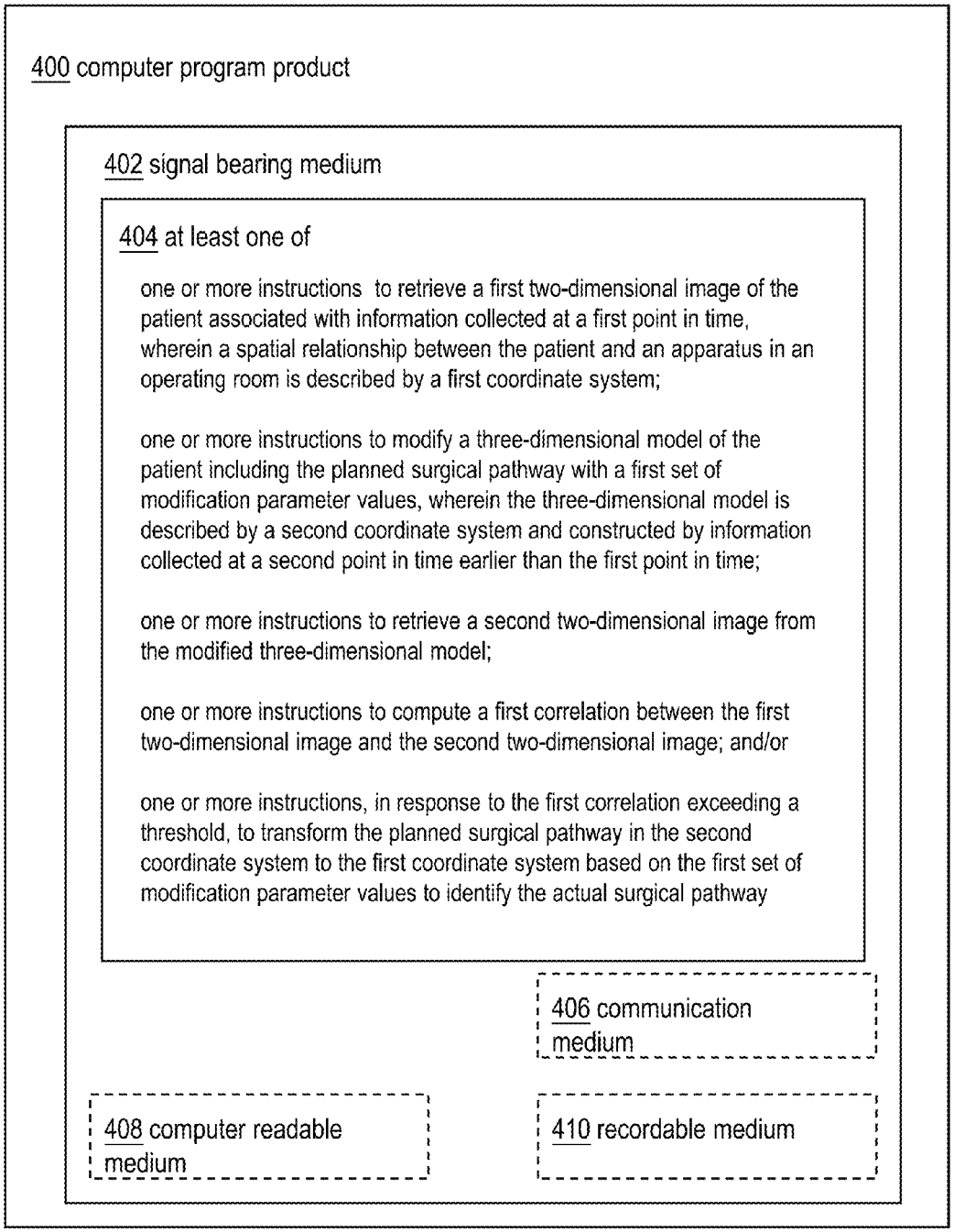
FIG. 4 is a block diagram illustrating a computer program product to implement a method to determine an actual surgical pathway, all arranged in accordance with some embodiments of the present disclosure.

FIG. 4 is a block diagram illustrating a computer program product 400 to implement a method to determine an actual surgical pathway, in accordance with one embodiment of the present disclosure. The computer program product 400 may include a signal bearing medium 402. Signal bearing medium 402 may include one or more sets of executable instructions 404 stored thereon that, in response to execution by, for example, the computing device 106 of FIG. 1, may provide the features and operations described above.

In some implementations, the signal bearing medium 402 may encompass a non-transitory computer readable medium 408, such as, but not limited to, a hard disk drive, a Compact Disc (CD), a Digital Versatile Disk (DVD), a digital tape, memory, etc. In some implementations, the signal bearing medium 402 may encompass a recordable medium 410, such as, but not limited to, memory, read/write (R/W) CDs, R/W DVDs, etc. In some implementations, signal bearing medium 402 may encompass a communications medium 406, such as, but not limited to, a digital and/or an analog communication medium (e.g., a fiber optic cable, a waveguide, a wired communications link, a wireless communication link, etc.).

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. A method to determine an actual surgical pathway of a patient based on a planned surgical pathway, comprising:
   retrieving a first two-dimensional image of the patient associated with information collected at a first point in time, wherein a spatial relationship between the patient and an apparatus in an operating room is described by a first coordinate system;
   modifying a three-dimensional model of the patient including the planned surgical pathway with a first set of modification parameter values, wherein the three-dimensional model is described by a second coordinate system and constructed by information collected at a second point in time earlier than the first point in time;
   retrieving a second two-dimensional image from the modified three-dimensional model;
   computing a first correlation between the first two-dimensional image and the second two-dimensional image; and
   in response to the first correlation exceeding a threshold, transforming the planned surgical pathway in the second coordinate system to the first coordinate system based on the first set of modification parameter values to determine the actual surgical pathway.

2. The method of claim 1, wherein the modifying the three-dimensional model includes scaling the three-dimensional model, rotating the three-dimensional model or moving the three-dimensional model based on the set of modification parameter values.

3. The method of claim 1, wherein the second two-dimensional image is a projection of the modified three-dimensional model.

4. The method of claim 1, wherein the patient is on an operating table in the operating room at the first point in time, and the patient is under a medical image scan at the second point in time.

5. The method of claim 1, in response to the first correlation not exceeding the threshold, further comprising:
   modifying the three-dimensional model of the patient including the planned surgical pathway with a second set of modification parameter values,
   retrieving a third two-dimensional image from the three-dimensional model modified with the second set of modification parameter values;
   computing a second correlation between the first two-dimensional image and the third two-dimensional image; and
   in response to the second correlation exceeding a threshold, transforming the planned surgical pathway in the second coordinate system to the first coordinate system based on the second set of modification parameter values to identify the actual surgical pathway.

6. The method of claim 1, further comprising performing edge detection on the first two-dimensional image and the second two-dimensional image.

7. The method of claim 6, wherein the edge detection is performed before the computation of the correlation.

8. A non-transitory computer-readable storage medium containing a set of executable instructions which, in response to execution by a processor in one of one or more surgical system, cause the processor to perform a method to determine an actual surgical pathway of a patient based on a planned surgical pathway, the method comprising:
   retrieving a first two-dimensional image of the patient associated with information collected at a first point in time, wherein a spatial relationship between the patient and an apparatus in an operating room is described by a first coordinate system;
   modifying a three-dimensional model of the patient including the planned surgical pathway with a first set of modification parameter values, wherein the three-dimensional model is described by a second coordinate system and constructed by information collected at a second point in time earlier than the first point in time;
   retrieving a second two-dimensional image from the modified three-dimensional model;
   computing a first correlation between the first two-dimensional image and the second two-dimensional image; and
   in response to the first correlation exceeding a threshold, transforming the planned surgical pathway in the second coordinate system to the first coordinate system based on the first set of modification parameter values to identify the actual surgical pathway.

9. The non-transitory computer-readable storage medium of claim 8, wherein the modifying the three-dimensional model includes scaling the three-dimensional model, rotating the three-dimensional model or moving the three-dimensional model based on the set of modification parameter values.

10. The non-transitory computer-readable storage medium of claim 8, wherein the second two-dimensional image is a projection of the modified three-dimensional model.

11. The non-transitory computer-readable storage medium of claim 8, wherein the patient is on an operating table in the operating room at the first point in time, and the patient is under a medical image scan at the second point in time.

12. The non-transitory computer-readable storage medium of claim 8, in response to the first correlation not exceeding the threshold, the method further comprising:
   modifying the three-dimensional model of the patient including the planned surgical pathway with a second set of modification parameter values,
   retrieving a third two-dimensional image from the three-dimensional model modified with the second set of modification parameter values;
   computing a second correlation between the first two-dimensional image and the third two-dimensional image; and
   in response to the second correlation exceeding a threshold, transforming the planned surgical pathway in the second coordinate system to the first coordinate system based on the second set of modification parameter values to identify the actual surgical pathway.

13. The non-transitory computer-readable storage medium of claim 8, the method further comprising performing edge detection on the first two-dimensional image and the second two-dimensional image.

14. The non-transitory computer-readable storage medium of claim 13, wherein the edge detection is performed before the computation of the correlation.

15. A surgical system configured to determine an actual surgical pathway of a patient based on a planned surgical pathway, comprising:
   a storage system;
   a robotic arm;
   an image collection apparatus; and
   a processor, wherein the processor is configured to
   retrieve a first two-dimensional image of the patient associated with information collected by the image collection apparatus at a first point in time from the storage system, wherein a spatial relationship between the patient and the robotic arm is described by a first coordinate system;
   modify a three-dimensional model of the patient including the planned surgical pathway with a first set of modification parameter values, wherein the three-dimensional model is described by a second coordinate system and constructed by information collected at a second point in time earlier than the first point in time;
   retrieve a second two-dimensional image from the modified three-dimensional model from the storage system;
   compute a first correlation between the first two-dimensional image and the second two-dimensional image;
   in response to the first correlation exceeding a threshold, transform the planned surgical pathway in the second coordinate system to the first coordinate system based on the first set of modification parameter values to identify the actual surgical pathway; and
   instruct the robotic arm to perform the surgery based on the actual surgical pathway.

16. The system of claim 15, wherein the three-dimensional model is modified with a scaling factor, a rotation degree, and/or a translation vector.

17. The system of claim 15, wherein the image collection apparatus is fixed with the robotic arm.

18. The system of claim 15, wherein the image collection apparatus is configured to take a plurality of images while the robotic arm is moving.

19. The system of claim 15, wherein the patient is on an operating table in the operating room at the first point in time, and the patient is under a medical image scan at the second point in time.

20. The system of claim 15, wherein the processor is further configured to perform an edge detection operation on the first two-dimensional image and the second two-dimensional image.

* * * * *

UNITED STATES PATENT AND TRADEMARK OFFICE
CERTIFICATE OF CORRECTION

PATENT NO. : 9,827,053 B2
APPLICATION NO. : 15/173512
DATED : November 28, 2017
INVENTOR(S) : Chieh-Hsiao Chen et al.

It is certified that error appears in the above-identified patent and that said Letters Patent is hereby corrected as shown below:

In the Specification

Column 8 at Line 2; the phrase "in which a represents a rotation" should read -- in which α represents a rotation --.

Signed and Sealed this
Twenty-fourth Day of July, 2018

Andrei Iancu
*Director of the United States Patent and Trademark Office*